(12) United States Patent
Boisson et al.

(10) Patent No.: US 9,598,510 B2
(45) Date of Patent: Mar. 21, 2017

(54) TELECHELIC POLYOLEFIN AND PREPARATION THEREOF

(71) Applicants: UNIVERSITE CLAUDE BERNARD LYON I, Villeurbanne (FR); CENTRE NATIONAL DE LA RECHERCHE SCIENTIFIQUE, Paris (FR); CPE LYON FORMATION CONTINUE ET RECHERCHE, Villeurbanne (FR)

(72) Inventors: Christophe Boisson, Tramoyes (FR); Franck D'Agosto, Villeurbanne (FR); Ian German, Bromsgrove (GB)

(73) Assignees: UNIVERSITE CLAUDE BERNARD LYON I, Villeurbanne (FR); CENTRE NATIONAL DE LA RECHERCHE SCIENTIFIQUE, Paris (FR); CPE LYON FORMATION CONTINUE ET RECHERCHE, Villeurbanne (FR)

( * ) Notice: Subject to any disclaimer, the term of this patent is extended or adjusted under 35 U.S.C. 154(b) by 0 days.

(21) Appl. No.: 14/383,404

(22) PCT Filed: Sep. 27, 2012

(86) PCT No.: PCT/EP2012/069110
§ 371 (c)(1),
(2) Date: Sep. 5, 2014

(87) PCT Pub. No.: WO2013/135314
PCT Pub. Date: Sep. 19, 2013

(65) Prior Publication Data
US 2015/0038647 A1 Feb. 5, 2015

(30) Foreign Application Priority Data

Mar. 12, 2012 (FR) .................... 12 52191

(51) Int. Cl.
| | | |
|---|---|---|
| *C07F 3/02* | (2006.01) | |
| *C08F 8/22* | (2006.01) | |
| *C08F 8/34* | (2006.01) | |
| *C08F 8/42* | (2006.01) | |
| *C07F 3/06* | (2006.01) | |
| *C07F 5/06* | (2006.01) | |
| *C08F 110/02* | (2006.01) | |
| *C08F 2/38* | (2006.01) | |
| *C08F 8/00* | (2006.01) | |
| *C08F 8/04* | (2006.01) | |
| *C08F 8/30* | (2006.01) | |

(52) U.S. Cl.
CPC .............. *C08F 8/42* (2013.01); *C07F 3/02* (2013.01); *C07F 3/06* (2013.01); *C07F 5/063* (2013.01); *C08F 2/38* (2013.01); *C08F 8/00* (2013.01); *C08F 8/04* (2013.01); *C08F 8/22* (2013.01); *C08F 8/30* (2013.01); *C08F 8/34* (2013.01); *C08F 110/02* (2013.01); *C08F 2810/40* (2013.01)

(58) Field of Classification Search
CPC .. C08F 110/02; C08F 2/38; C08F 8/42; C08F 2810/40; C07F 3/06; C07F 5/063
See application file for complete search history.

(56) References Cited

U.S. PATENT DOCUMENTS

| | | | | |
|---|---|---|---|---|
| 6,274,688 B1 * | 8/2001 | Nakagawa | ................ | C08F 2/38 |
| | | | | 526/328 |
| 2004/0030048 A1 | 2/2004 | Letchford | | |
| 2007/0010639 A1 | 1/2007 | Makio et al. | | |
| 2010/0004393 A1 * | 1/2010 | Ikenaga | .................... | B32B 1/02 |
| | | | | 525/55 |

OTHER PUBLICATIONS

Yagci, Y. et al. Telechelic Polymers. Encyclopedia of Polymer Science and Technology p. 64 published online Jul. 2004.*
Mazzolini J. et al: "Catalyzed chain growth (CCG) on a main group metal: an efficient tool to functionalize polyethylene," Polymer Chemistry, vol. 1, Jan. 22, 2010, pp. 793-800.
Unterlass, M. et al: "Polyethylenes bearing a terminal porphyrin group," Chemical Communications, vol. 47, 2011, pp. 7057-7059.
Espinosa, E. et al: "Synthesis of Cyclopentadienyl Capped Polyethylene and Subsequent Block Copolymer Formation Via Hetero Diels-Alder (HDA) Chemistry," Macromolecular Rapid Communications, vol. 32, 2011, pp. 1447-1453.
Gottfried, A. et al: "Living and Block Copolymerization of Ethylene and α-Olefins Using Palladium(II)—α-Diimine Catalysts," Macromolecules, vol. 36, 2003, pp. 3085-3100.
Gibson, V. et al: "Advances in Non-Metallocene Olefin Polymerization Catalysts," Chemical Reviews, vol. 103, 2004, pp. 283-315.
Briquel R. et al: "Polyethylene Building Blocks by Catalyzed Chain Growth and Efficient End Functionalization Strategies, Including Click Chemistry," Angewandte Chemie, vol. 47, 2008, pp. 9311-9313.
Mazzolini J. et al: "Thiol-End-Functionalized Polyethylenes," Macromolecules, vol. 43, 2010, pp. 7495-7503.

(Continued)

*Primary Examiner* — Irina S Zemel
*Assistant Examiner* — Jeffrey Lenihan
(74) *Attorney, Agent, or Firm* — Heslin Rothenberg Farley & Mesiti P.C.

(57) ABSTRACT

Telechelic polyolefin of formula(I) and its derivatives:

$$CH_2=CH-(CH_2)_p-A-Z \qquad (I)$$

wherein:
A represents a (co)polymer comprising at least 95 mol % of ($CH_2$—$CH_2$) units;
Z is selected from the group comprising halogens, thiols and their derivatives, azides, amines, alcohols, the carboxylic acid function, isocyanates, silanes, phosphorous derivatives, dithioesters, dithiocarbamates, dithiocarbonates, trithiocarbonates, alkoxyamines, the vinyl function, dienes, and the group -A-$(CH_2)_p$—$CH=CH_2$;
p is a whole number between 1 and 20, most advantageously between 6 and 9.

17 Claims, 3 Drawing Sheets

(56) References Cited

OTHER PUBLICATIONS

Fraser C. et al: "Degradable Cyclooctadiene/Acetal Copolymers: Versatile Precursors to 1,4-Hydroxytelechelic Polybutadiene and Hydroxytelechelic Polyethylene," Macromolecules vol. 28, 1995, pp. 7256-7261.
Mazzolini, J. et al: "Polyethylene End Functionalization Using Radical-Mediated Thiol-Ene Chemistry: Use of Polyethylenes Containing Alkene End Functionality." Macromolecules, vol. 44, 2011, pp. 3381-3387.
International Search Report for PCT/EP2012/069110 dated Oct. 19, 2012.

\* cited by examiner

TELECHELIC POLYOLEFIN AND PREPARATION THEREOF

CROSS REFERENCE TO RELATED APPLICATIONS

This application is a national stage filing under section 371 of International Application No. PCT/EP2012/069110, filed on Sep. 27, 2012, and published on Sep. 19, 2013 as WO 2013/135314 A1, which claims priority to French Application No. 1252191, filed on Mar. 12, 2012. The entire contents of said applications are hereby incorporated herein by reference.

FIELD OF THE INVENTION

The invention described herein concerns a telechelic polyolefin presenting a reactive group at each polymer chain-end. This type of polymer can serve as a precursor for the incorporation of the polymer into e.g. a hydrophilic or hydrophobic environment, or organic, inorganic, hybrid or composite materials.

STATE OF THE ART

In general, a polymer able to undergo a subsequent polymerization or reaction in light of the reactivity of its chain-ends is known as a "telechelic polymer". In this class of molecule, the reactive groups located at the chain-ends do not originate from the monomers.

The prior art includes mono-functionalized polyethylene (see for instance Mazzonlini et al. Polymer Chemistry, 2010, 1, 793-800). There is no evident chemistry to obtain telechelic polyethylene from these mono-functionalized polyethylenes.

Many synthetic routes to telechelic polymers have been described in the literature. However, regarding the synthesis of telechelic polyolefin synthesis, three principle methods have been developed:

(i) The first concerns the synthesis of a hydroxyl-telechelic polybutadiene by an anionic pathway. The butadiene is first polymerized before a hydrogenation step of the unsaturated groups of the polymer chain. The telechelic polyethylene thus obtained features identical chain-ends and is also branched due to the presence of ethyl groups resulting from 1,2-butadiene enchainment. This type of polymer is commercially available under the trade name Kraton® L2203. Document US 2004/0030048 describes a polymer having chain-end groups such as OH, SH or an amine. It does not concern bi-functionalized polyethylene polymers.

(ii) Another synthetic pathway concerns the polymerization of cyclooctadiene by ring-opening metathesis polymerization (ROMP). The polymer obtained is then hydrogenated to give a hydroxyl-telechelic polyolefin (Hillmyer et al. Macromolecules 1995, 28, 7256-7261).

(iii) Finally living ethylene polymerization has also been demonstrated in the presence of a palladium complex. This complex not only initiates the living polymerization of ethylene, but also acts as a chain-end functionalization reagent. The branched, telechelic polyethylene obtained features chain-end functions of either identical ester groups, or those of one ester function and one ketone function (Brookhart, Macromolecules 2003, 36, 3085). In the same vein, the document US2007/0010639 describes the three-step synthesis of telechelic polypropylene featuring polar chain-ends. Olefinic monomers containing protected functional groups are used at the start of the polymerization to create a short segment with orthogonal functional groups. The (co)polymerization of polypropylene is then undertaken. Following that, a functional monomer is again used to form a second short sequence containing lateral functional groups. The polymers thus prepared are free from vinyl groups at the chain-end.

With the term "living polymerization" we denote a chain-growth polymerization that does not include transfer reactions or chain-termination reactions. Living polymerizations of olefins allow the preparation of polymers that are functional at one or two chain-ends. In the field of olefin polymerization however, living polymerization is limited by the fact that only one chain may be produced per transition metal complex, which poses a problem in terms of production cost. Catalytic polymerization presents the advantage of producing a large number of chains per transition metal. There is therefore a need to establish a system permitting the preparation of telechelic polyolefins, particularly polyethylene, in true polymerization conditions by coordination catalysis.

The problem proposed to be solved by the invention described herein concerns the preparation of a polymer, in particular telechelic polyolefin of which the two principal chain-ends are either identical or non-identical.

In contrast to the literature procedures, the procedure of this invention permits the catalytic polymerization of an olefin (mono-olefin) by a mechanism that results in a large number of chains produced per catalyst molecule; and that polymerization proceeds in a controlled fashion in the sense that the distribution of molecular weight of the polymer chains produced is narrow ($M_w/M_n<1.5$) and that molecular weight increases with productivity.

This process for polymerization and functionalization can be implemented in situ. It is not necessary to isolate an intermediate to ensure the functionalization of the chain-ends.

SUMMARY OF THE INVENTION

The applicant has developed a polyolefin of which the two chain-ends each feature a functional group. It is a polyolefin in which at least one of the chain-ends is readily reacted to facilitate the incorporation of the described polyolefin into e.g. a hydrophilic or hydrophobic environment, or into organic, inorganic, hybrid or composite materials.

The telechelic polyolefin according to the invention is preferably linear. It includes, advantageously, two distinct chain-ends, able to react selectively due to their different reactivity.

More specifically, the subject matter of the present invention concerns a telechelic polyolefin of formula (I) and its derivatives:

$$CH_2=CH-(CH_2)_p-A-Z \qquad (I)$$

wherein:
- A represents a (co)polymer comprising at least 95 mol % of ($CH_2-CH_2$) units,
- Z is a functional group selected from the group comprising halogens; thiols and their derivatives; azides; amines; alcohols; carboxylic acid function; isocyanates; silanes; phosphorous derivatives; dithioesters; dithiocarbamates; dithiocarbonates; trithiocarbonates; alkoxyamines; vinyl function; dienes; and the group A-$(CH_2)_p$-CH=$CH_2$;
- p is a whole number between 1 and 20, preferably between 6 and 9.

The term 'derivatives of the telechelic polyolefin' of formula (I) is defined as all polyolefins resulting from the functionalization of at least one of the chain-ends of the telechelic polyolefin of formula (I). Derivatives are therefore the products obtained from the modification of at least one of the vinyl function or the group Z, and preferentially of the vinyl function according to reactions known to the skilled man in the art.

The units ($CH_2$—$CH_2$) of the (co)polymer A originate from the polymerization of ethylene.

Generally, polymer A is a linear polyethylene or a linear copolymer of ethylene with at least one alpha-olefin containing at least one unsaturated bond. As previously described, this (co)polymer is comprised of at least 95% by mole fraction of ($CH_2$—$CH_2$) units.

However, according to a preferred embodiment, polymer A is a linear polyethylene, i.e. a homopolymer of ethylene of formula ($CH_2$—$CH_2$)$_n$, n being a whole number between 7 and 3600, advantageously between 17 and 360.

The (co)polymer A has preferably an average molar mass of between 200 g/mol and 100,000 g/mol, most advantageously between 500 g/mol and 10,000 g/mol.

According to a particularly preferred embodiment, group Z in the telechelic polyolefin of formula (I) is a halogen—preferably an iodine atom or a dithiocarbamate group.

The principal chain-ends of the telechelic polyolefin of formula (I) may feature two groups, in this case vinyl and Z, of which the respective reactivity of one is significantly different from the other.

Consequently, according to a particularly preferred embodiment, the telechelic polyolefin is of the formula $CH_2$=CH—$(CH_2)_p$-A-Z, Z being an iodine atom or dithiocarbamate group and p being a whole number between 6 and 9. Advantageously, the (co) polymer A is polyethylene, ($CH_2$—$CH_2$), n being a whole number between 7 and 3600, preferably between 17 and 360.

The present invention also concerns a process for preparing a telechelic polyolefin of formula (I), $CH_2$=CH—$(CH_2)_p$-A-Z, and its derivatives. This procedure is characterized in that it comprises in particular the following steps:

preparation of a compound of formula (II):

$$Y(A\text{-}(CH_2)_p\text{—}CH\text{=}CH_2)_m \qquad (II)$$

in which when m=2, Y is an alkaline earth atom, preferentially magnesium, or zinc;
and when m=3, Y is an element of group 13, preferably aluminium
cleavage of the bond(s) between Y and A-$(CH_2)_p$—CH=$CH_2$, and functionalization of A-$(CH_2)_p$—CH=$CH_2$ with Z.

The preparation of the molecule of composition of formula (II) is effected in the presence of a complex of a transition metal or a lanthanide, and a transfer agent of composition described by formula (III):

$$Y((CH_2)_p\text{—}CH\text{=}CH_2)_m \qquad (III)$$

As previously described, the group Z may be chosen from a selection including halogens, thiols and their derivatives, azides, amines, alcohols, carboxylic acid function, isocyanates, silanes, phosphorous derivatives, dithioesters, dithiocarbamates, dithiocarbonates, trithiocarbonates, alkoxyamines, vinyl function, dienes and the group A-$(CH_2)_p$—CH=$CH_2$.

According to a preferred embodiment, the group Z is an iodine atom or a dithiocarbamate group, such as diethyldithiocarbamate (S—C(=S)—N(Et)$_2$.

The complex of a transition metal or a lanthanide is preferably a metallocene, selected from the group comprising compounds of which the formula contains the base structure: $(Cp^1)(Cp^2)M$ or $E(Cp^1)(Cp^2)M$.

This complex allows the implementation of catalytic olefin polymerization by coordination-insertion, with a large number of chains produced per catalyst molecule.

Generally, M is a metal from group 3 or 4, or a lanthanide.
Furthermore, $Cp^1$, $Cp^2$ are cyclopentadienyl, fluorenyl or indenyl groups, which may be substituted.

Group E is a bridge between the $Cp^1$ and $Cp^2$ ligands, and can be represented by the formula M'$R^1R^2$ in which M' is an element from group 14; $R^1$ and $R^2$ are either identical or non-identical and chosen from the group comprising alkyl and aryl groups having between 1 and 20 carbon atoms. Group E may, for example, be —C($CH_3$)$_2$—, —$CH_2$—$CH_2$—, or —Si($CH_3$)$_2$—.

The transition metal or lanthanide complex may also be of a non-metallocene structure, such as those described in the review of V. C. Gibson and S. K. Spitzmesser (*Chem. Rev.* 2003, 103, 283-315).

Where appropriate, particularly when the complex does not include a lanthanide or group 3 metal, a co-catalyst may be used in combination with the complex. The skilled man in the art will be able to choose the appropriate co-catalyst.

According to particularly preferred embodiment, the metallocene complex is of the formula $(C_5Me_5)_2MX_2Li(OEt_2)_2$, M being a lanthanide or group 3 metal and X being preferentially a halogen. It is preferably a lanthanide complex, most advantageously one of Nd, and notably of the structure $(C_5Me_5)_2NdCl_2Li(OEt_2)_2$.

In the second step of the procedure of the invention, the functionalization with Z can be effected by the addition of a compound which may notably be chosen from the group comprising iodine; sulfur —$S_8$; oxygen; nitroxyl radicals; $CO_2$; chlorosilanes, such as Cl$SiR_2$H or $Cl_2$SiRH (R being an alkyl group containing between 1 and 20 carbon atoms); isobutene; alkyl halides, aryl halides and vinyl halides; $CS_2$; and disulfides such as tetraethylthiuram disulfide.

The functionalization step is preferably carried out by addition of iodine $I_2$, sulfur $S_8$ or tetraethylthiuram disulfide.

The second step of the procedure consists in introducing the Z group by cleavage of the Y-A bond, of the intermediate complex of formula (II), formed during the olefin polymerization in the presence of the transfer agent and the transition metal or lanthanide complex.

Consequently, the polyolefin of formula $CH_2$=CH—$(CH_2)_p$-A-I may serve as a precursor to new polyolefins, for example polyolefins including a Z group of the type azide ($N_3$) or amine ($NH_2$).

According to a particular embodiment, the functionalization step with Z may proceed via oxidative coupling, to obtain a polyolefin of the formula $CH_2$=CH—$(CH_2)_p$-A-A-$(CH_2)_p$—CH=$CH_2$, i.e. a polyolefin where the group Z has the structure -A-$(CH_2)_p$—CH=$CH_2$.

This oxidative coupling reaction can be implemented by the reaction of the intermediate complex $Y(A\text{-}(CH_2)_p$—CH=$CH_2)_m$, notably in the presence of a silver tosylate catalyst. This is particularly the case when Y—Mg.

One of the advantages of the process that is the subject matter of the invention is that all steps may be performed in situ. Unlike procedures outlined in the prior art that concern telechelic polyolefins, the procedure described herein eliminates the separation steps for intermediate compounds in that the second step can be carried out in situ. The polymerization and functionalization can therefore be advantageously achieved in the same reactor.

Furthermore, the polymerization displays pseudo-living characteristics which permits the control of the polymer molar mass and provides for a relatively narrow polymer molecular weight distribution, advantageously with $M_w/M_n < 1.5$.

Generally, the experimental conditions allow control of the molar mass of the telechelic polyolefin of formula (I), in addition to the level of chain-end functionalization of (I) with the groups vinyl and Z. The level of functionalization is approximated using % F:

% F=100×[number of vinyl chain-end groups per chain]×[number of Z chain-end groups per chain], with the maximum number of vinyl chain-ends per chain being fixed at 1.

The number of vinyl and/or Z chain-ends present are determined by NMR (nuclear magnetic resonance) spectroscopy, according to techniques known to the skilled man in the art.

The level of functionalization can thus be advantageously greater than 70% and most advantageously greater than 90%. In short, the process according to the invention allows the advantageous production of at least 90% telechelic polyolefins.

Furthermore, this procedure allows the direct polymerization of ethylene, a monomer considerably less expensive than butadiene or cyclooctadiene, monomers featured in prior art routes to telechelic polyolefins.

The chain transfer agent of formula (III) (preferably when m=2 and Y=alkaline earth metal) and its usage (when m=2 or 3) in a process for the preparation of telechelic polyethylene also fall under the invention described herein.

As previously outlined, according to a particular embodiment, the telechelic polyolefin which is the subject matter of the invention is of the formula $CH_2=CH-(CH_2)_p-(CH_2-CH_2)_n-I$, I being an iodine atom, p being a whole number between 6 and 9, and n being a whole number between 17 and 360. This polymer can advantageously be obtained according to the procedure comprising the following steps:
  preparation of the compound of formula (II) (with Z=I; p=9; n=17 to 360) by polymerization of ethylene, $CH_2=CH_2$, in the presence of $(C_5Me_5)_2NdX_2Li(OEt_2)_2$, X being a halogen, and the transfer agent $Mg((CH_2)_9-CH=CH_2)_2$;
  functionalization by the addition of iodine in order to obtain the telechelic polyolefin $CH_2=CH-(CH_2)_9-(CH_2-CH_2)_n-I$.

The derivatives of the telechelic polyolefin of formula (I) may, as previously outlined, be obtained by the above procedure, notably by the modification of at least one chain-end of the telechelic polyolefin in a step subsequent to functionalization with Z. At least one of the chain-ends of the telechelic polyolefin can therefore be modified by reaction of the vinyl function and/or of the Z group.

With regard to the vinyl and Z groups of the telechelic polyolefin of formula (I), the two groups may later be readily modified by organic chemistry to introduce new groups, whether by transformation of the Z group or of the vinyl group, as has been detailed for monofunctional polyethylene by D'Agosto and Boisson et al. (R. Briquel, J. Mazzolini, T. Le Bris, O. Boyron, F. Boisson, F. Delolme, F. D'Agosto, C. Boisson, R. Spitz *Angew. Chem. Int. Eng. Ed.*, 47, 9311-9313 (2008); J. Mazzolini, R. Briquel, I. Mokthari, O. Boyron, V. Monteil, F. Delolme, D. Gigmes, D. Bertin, F. D'Agosto, C. Boisson *Macromolecules* 43, 7495-7503 (2010); M. Unterlass, E. Espinosa, F. Boisson, F. D'Agosto, C. Boisson, K. Ariga, I. Khalakhan, R. Charvet, J P. Hill *Chem. Commun.* 47, 7057-7059 (2011); Mazzolini, O. Boyron, V. Monteil, D. Gigmes, D. Bertin, F. D'Agosto, C. Boisson *Macromolecules* 44, 3381-3387 (2011); E. Espinosa, M. Glassner, C. Boisson, C. Barner Kowollik, F. D'Agosto *Macromol. Rapid Commun.* 32, 1447-1453 (2011)).

The telechelic polyolefin of formula (I), $CH_2=CH-(CH_2)_p-A-Z$, can therefore be later modified. The skilled man in the art will be able to selectively modify the vinyl function. One could, in particular, although not limitatively, refer to the reactions described in the document Macromolecules 44, 3381-3387 (2011).

The present invention therefore also concerns the derivatives of the telechelic polyolefin of formula (I).

Additionally, the present invention concerns the utilization of telechelic polyolefins and their derivatives as additive(s) for the modification of organic, inorganic, hybrid or composite materials, or as reactive synthon(s) for polymerization reactions in the role of initiator, monomer, transfer agent, deactivation/termination agent, control agent or crosslinking agent.

The fields of interest for the present invention concern in particular, yet are not limited to, cosmetics, adhesives, inks, waxes and coatings.

The telechelic polyolefins of the invention and their derivatives may be applied within the framework of the preparation of architectures or of original materials based on polyethylene in particular.

The invention, and the benefits which result from it, is best described by the following examples, given to illustrate the invention and which are not limitative of the scope of the invention.

FIGURES

EXAMPLES

Figure 1:
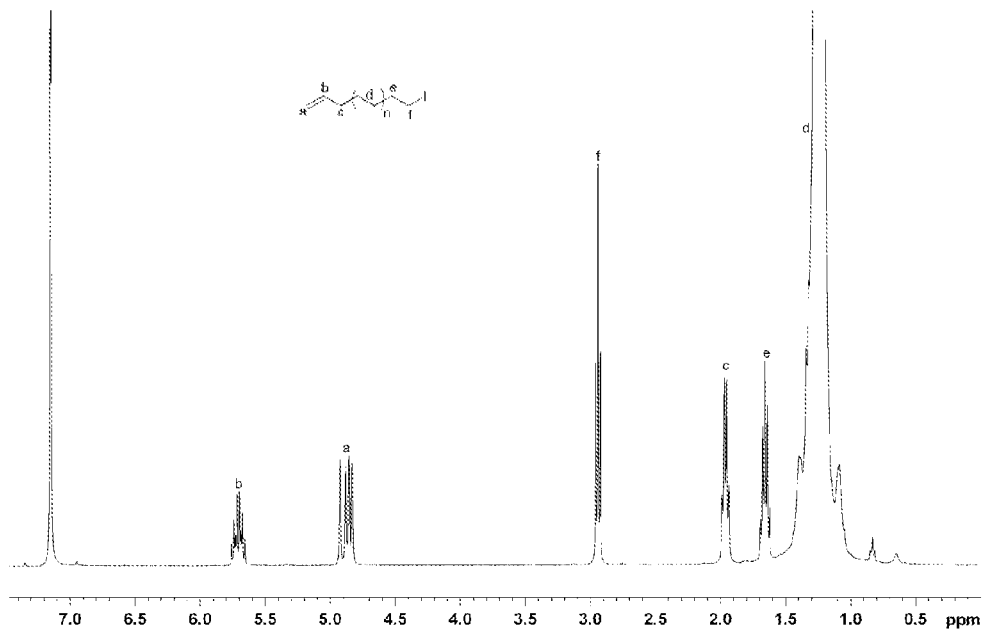
FIG. 1 is the $^1$H NMR (nuclear magnetic resonance) spectrum of the telechelic polyethylene according to the invention, $CH_2=CH-(CH_2)_9-PE-I$, where $PE=(CH_2-CH_2)$.

The following examples concern the preparation:
of a transfer agent of formula (III)
of an intermediate compound of formula (II);
of telechelic polyolefins of formula (I).

Synthesis of the Transfer Agent bis(10-undecenyl) magnesium, $Mg((CH_2)_9CH=CH_2)_2$ To a suspension of magnesium (2.38 g, 98 mmol) in di-n-butyl ether (100 ml) was added 11-bromo-1-undecene (11.3 ml, 49 mmol) dropwise at 0° C. The reaction mixture was stirred at 0° C. for 1 h and then allowed to return to room temperature. The resulting suspension was filtered to remove excess magnesium. To the filtrate was added dioxane (5.0 ml, 59 mmol), whereupon a white precipitate was immediately formed. The suspension was stirred for 2 h and then filtered, to obtain a solution of $Mg((CH_2)_9CH=CH_2)_2$ in di-n-butyl ether.

Aliquots from the solution were taken for concentration determination by titration using i) pyrene-1-acetic acid and ii) $HCl_{(aq)}$ then $NaOH_{(aq)}$ solutions.

A further sample of the recovered solution was taken and the solvent removed under reduced pressure for NMR analysis.

Characterization by $^1H$ NMR (THF-$d_8$, 300 MHz, 300K) δ: 5.81 (m, $CH_2=CH-CH_2-$), 4.89-5.02 (m, $CH_2=CH-CH_2-$), 2.06 (q, J=7 Hz, $CH_2=CH-CH_2-$), 1.56 (quin, J=7 Hz, 1.32 (br, $-(CH_2)_6-$), −0.63 (m, $-CH_2-Mg$) ppm.

General Polymerization Procedure for the Preparation of the Intermediate $CH_2=CH-(CH_2)_9-PE-Mg-PE-(CH_2)_9-CH=CH_2 (PE=(CH_2-CH_2)_n)$ A solution of bis(10-undecenyl)magnesium in dibutyl ether (0.24 mol·L$^{-1}$, 10.4 ml, 2.5 mmol) was diluted with toluene (400 mL). The resulting solution was transferred to a reactor under an argon atmosphere. The reactor was heated to 75° C. and then charged with an ethylene atmosphere at a pressure of 3 bars. A precatalyst suspension of $Cp*_2NdCl_2Li(OEt_2)_2$ (10.7 mg, 16.7 μmol) in toluene (10 ml) was then added to the reactor and the consumption of ethylene monitored. After the desired consumption the ethylene atmosphere was replaced with argon.

Synthesis of the telechelic polyolefin $CH_2=CH-(CH_2)_9-PE-I$ $(PE=(CH_2-CH_2)_n)$ After the polymerization step described above, the reaction mixture containing the intermediate $CH_2=CH-(CH_2)_9-PE-Mg-PE-(CH_2)_9-CH=CH_2$ $(PE=(CH_2-CH_2)_n)$ was cooled to 10° C.

A solution of iodine (2.54 g, 10 mmol) in 50 mL of THF was added, and the suspension stirred for 3 hours.

The reactor contents were then added to methanol (200 mL) and the solution filtered. The solids recovered were washed with methanol (3×100 mL) then dried.
Characterization:

$^1H$ NMR (FIG. 1) (2/1 v/v TCE/$C_6D_6$, 400 MHz, 363K) δ ppm=5.70 (m, $CH_2=CH-CH_2-$), 4.83-4.93 (m, $CH_2=CH-CH_2-$), 2.94 (t, J=7 Hz, $-CH_2I$), 1.96 (q, J=7 Hz, $CH_2=CH-CH_2-$), 1.66 (quin, J=7 Hz, $-CH_2CH_2I$), 1.24 (br, $(CH_2CH_2)_n$).

$^{13}C$ NMR (2/1 v/v TCE/$C_6D_6$, 101 MHz, 363K) δ ppm=138.90, 114.20, 33.98, 30.78, 30.00 $((CH_2CH_2)_n)$, 29.90, 29.82, 29.80, 29.69, 29.44, 29.32, 28.82, 4.96.

$M_n$=1500 g·mol$^{-1}$, $M_w/M_n$=1.1, F=95%.

Synthesis of the Telechelic Polyolefin $CH_2=CH-(CH_2)_9-PE-S-C(=S)-N(Et)_2$ $(PE=(CH_2-CH_2)_n)$ After the polymerization step described above, the reaction mixture containing the intermediate $CH_2=CH-(CH_2)_9-PE-Mg-PE-(CH_2)_9-CH=CH_2$ $(PE=(CH_2-CH_2)_n)$ was heated to 80° C.

A solution of N,N,N',N'-tetraethylthiuram disulfide (1.85 g, 6.25 mmol) in toluene (50 mL) was then added and the resulting solution stirred for 3 hours.

The reaction mixture was cooled to ambient temperature before being added to methanol (200 mL), then the resulting suspension filtered.

Figure 2:
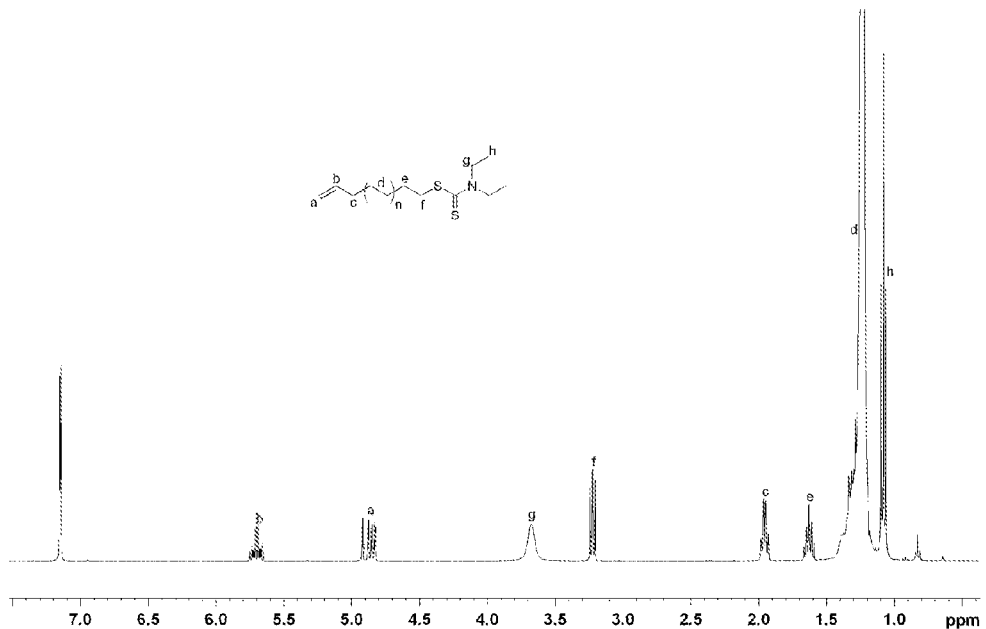
FIG. 2 is the $^1$H NMR (nuclear magnetic resonance) spectrum of the telechelic polyethylene according to the invention, $CH_2=CH-(CH_2)_9-PE-S-C(=S)-N(Et)_2$, where $PE=(CH_2-CH_2)$.

The solids recovered from filtration were washed three times with methanol (3×100 mL) then dried.
Characterization:

$^1H$ NMR (FIG. 2) (2/1 v/v TCE/$C_6D_6$, 400 MHz, 363K) δ ppm=5.70 (m, $CH_2=CH-CH_2-$), 4.83-4.93 (m, $CH_2=CH-CH_2-$), 3.68 (br, $-N-CH_2-CH_3$), 3.23 (t, J=7 Hz, $-CH_2-S-C(S)-$), 1.96 (q, J=7 Hz, $CH_2=CH-CH_2-$), 1.63 (quin, J=7 Hz, $-CH_2CH_2-S-C(S)-$) 1.24 (br, $(CH_2CH_2)_n$), 1.08 (t, J=7 Hz, $-N-CH_2-CH_3$).

$^{13}C$ NMR (2/1 v/v TCE/$C_6D_6$, 101 MHz, 363K) δ ppm=195.98, 138.90, 114.20, 47.74, 37.38, 33.98, 30.0 $((CH_2CH_2)_n)$, 29.90, 29.83, 29.80, 29.54, 29.44, 29.35, 29.32, 29.23, 12.25.

$M_n$=1550 g·mol$^{-1}$, $M_w/M_n$=1.14, F=87%

Synthesis of the Telechelic Polyolefin $CH_2=CH-(CH_2)_9-PE-SH$ $(PE=(CH_2-CH_2)_n)$ A suspension of lithium aluminium hydride (0.61 g, 16 mmol) in tetrahydrofuran (200 mL) was added to a solution of $CH_2=CH-(CH_2)_9-PE-S-C(=S)-NEt_2$ ($M_n$=1550 g·mol$^{-1}$, F=87%; 3.0 g) in toluene (200 mL) at 100° C.

The suspension obtained was stirred under argon in reflux conditions (90° C.) for 15 hours.

The reaction mixture was then cooled to ambient temperature, at which point methanol (20 mL) was slowly added.

The resultant suspension was then heated to 95° C. and filtered.

The filtrate was cooled and added to methanol (200 mL).

The suspension produced was then filtered and the solids recovered were washed with methanol (3×100 mL) and dried under vacuum.

Yield=2.5 g.
Characterization:

$^1H$ NMR (2/1 v/v TCE/$C_6D_6$, 400 MHz, 363K): δ ppm=5.70 (m, $CH_2=CH-CH_2-$), 4.83-4.93 (m, $CH_2=CH-CH_2-$), 2.32 (t, J=7 Hz, $-CH_2SH$), 1.96 (q, J=7 Hz, $CH_2=CH-CH_2-$), 1.24 (br, $(CH_2CH_2)_n$), 1.05 (t, J=7 Hz, $-CH_2SH$).

F=70%

Synthesis of the Telechelic Polyolefin $CH_2=CH-(CH_2)_9-PE-N_3$ $(PE=(CH_2-CH_2)_n)$ To a suspension of $CH_2=CH-(CH_2)_9-PE-I$ $(PE=(CH_2-CH_2)_n)$ in toluene was added sodium azide (1,2 equivalents). A mixture of toluene and DMF was added, then the reaction mixture heated to 120° C. and stirred for 3 hours.

The reactor contents were then added to methanol (200 mL) and the resultant suspension filtered.

Figure 3:
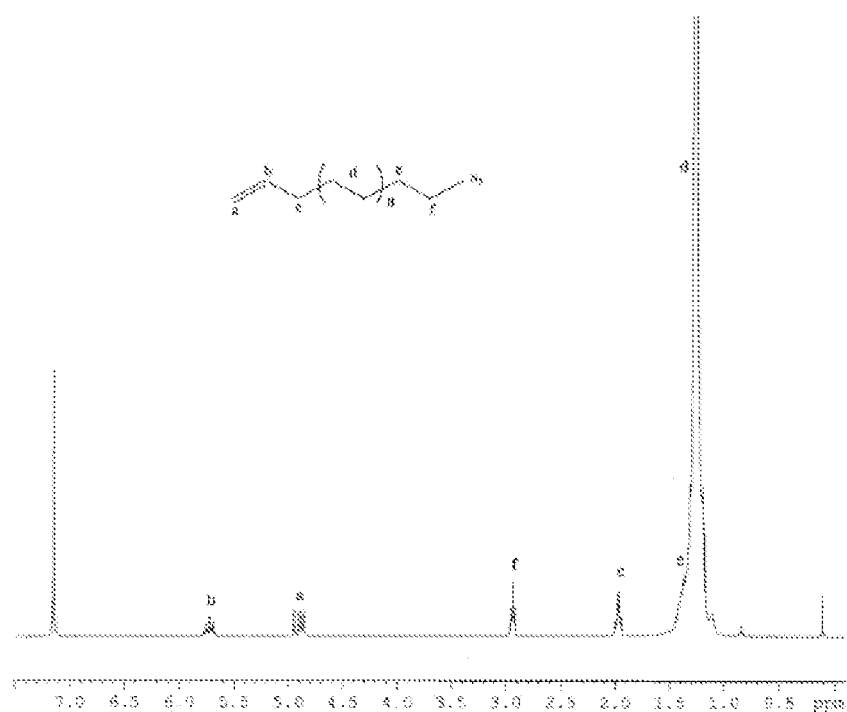
FIG. 3 is the $^1$H NMR (nuclear magnetic resonance) spectrum of the telechelic polyethylene according to the invention, $CH_2=CH-(CH_2)_9-PE-N_3$, where $PE=(CH_2-CH_2)$.

The solids recovered were washed with methanol (3×100 mL) and dried.
Characterization:

$^1H$ NMR (FIG. 3) (2/1 v/v TCE/$C_6D_6$, 400 MHz, 363K) δ ppm=5.70 (m, $CH_2=CH-CH_2-$), 4.83-4.93 (m, $CH_2=CH-CH_2-$), 3.00 (t, J=7 Hz, $-CH_2N_3$), 1.96 (q, J=7 Hz, $CH_2=CH-CH_2-$), 1.72 (quin, J=7 Hz, $-CH_2CH_2N_3$), 1.24 (br, $(CH_2CH_2)_n$)

Synthesis 1: $M_n$=1080 g·mol$^{-1}$, $M_w/M_n$=1.1, F=94%. For this synthesis, 3 g of $CH_2=CH-(CH_2)_9-PE-I$ ($M_n$=1080 g·mol$^{-1}$, F=94%) were used.

Synthesis 2: $M_n$=1750 g·mol$^{-1}$, $M_w/M_n$=1.2, F=89%. For this synthesis, 3 g of CH$_2$=CH—(CH$_2$)$_9$-PE-I ($M_n$=1750 g·mol$^{-1}$, F=90%) were used.

Synthesis of the Telechelic Polyolefin CH$_2$=CH—(CH$_2$)$_9$-PE-NH$_2$ (PE=(CH$_2$—CH$_2$)$_n$)

To a suspension of CH$_2$=CH—(CH$_2$)$_9$-PE-N$_3$ (PE=(CH$_2$—CH$_2$)$_n$) (1.5 g, $M_n$=1750 g·mol$^{-1}$, F=89%) in 100 mL of toluene was added a solution of lithium aluminium hydride (LiAlH$_4$, 10 equivalents) in 50 mL of THF. The suspension was stirred at 100° C. for 6 hours.

The reactor contents were then added to methanol (200 mL) and the suspension obtained was filtered.

The solids recovered were washed with methanol (3×100 mL) and dried.

Figure 4:
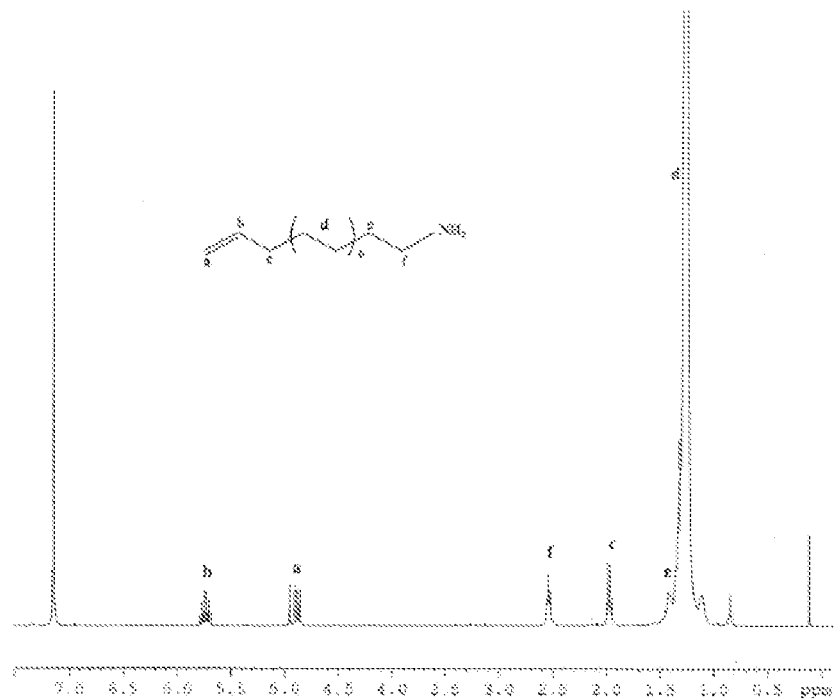
FIG. 4 is the $^1$H NMR (nuclear magnetic resonance) spectrum of the telechelic polyethylene according to the invention, $CH_2=CH-(CH_2)_9-PE-NH_2$, where $PE=(CH_2-CH_2)$.

Characterization:

$^1$H NMR (FIG. 4) (2/1 v/v TCE/C$_6$D$_6$, 400 MHz, 363K) δ ppm=5.70 (m, CH$_2$=CH—CH$_2$—), 4.83-4.93 (m, CH$_2$=CH—CH$_2$—), 2.55 (t, J=7 Hz, —CH$_2$NH$_2$), 1.96 (q, J=7 Hz, CH$_2$=CH—CH$_2$—), 1.47 (quin, J=7 Hz, —CH$_2$CH$_2$NH$_2$), 1.24 (br, (CH$_2$CH$_2$)$_n$).

Synthesis 1: $M_n$=1750 g·mol$^{-1}$, $M_w/M_n$=1.2, F=85%.

Synthesis of the Telechelic Polyolefin CH$_2$=CH—(CH$_2$)$_9$-PE-(CH$_2$)$_9$—CH=CH$_2$ (PE=(CH$_2$—CH$_2$)$_n$) by Oxidative Homo-Coupling After the general polymerization procedure described above, the temperature of the reaction mixture containing the intermediate CH$_2$=CH—(CH$_2$)$_9$-PE-Mg-PE-(CH$_2$)$_9$—CH=CH$_2$ was maintained at 80° C.

A solution of silver tosylate (2 mol % with respect to CH$_2$=CH—(CH$_2$)$_9$-PE-Mg-PE-(CH$_2$)$_9$—CH=CH$_2$(PE=(CH$_2$—CH$_2$)$_n$) and 1,2-dibromoethane (2,4 equivalents with respect to CH$_2$=CH—(CH$_2$)$_9$-PE-Mg-PE-(CH$_2$)$_9$—CH=CH$_2$ (PE=(CH$_2$—CH$_2$)$_n$) in THF (40 mL) was added to the post-polymerization reaction mixture. The resultant suspension was stirred for 16 hours.

The reactor contents were then added to methanol (200 mL) and the suspension obtained was filtered.

The solids recovered were washed with methanol (3×100 mL) and dried.

Figure 5:
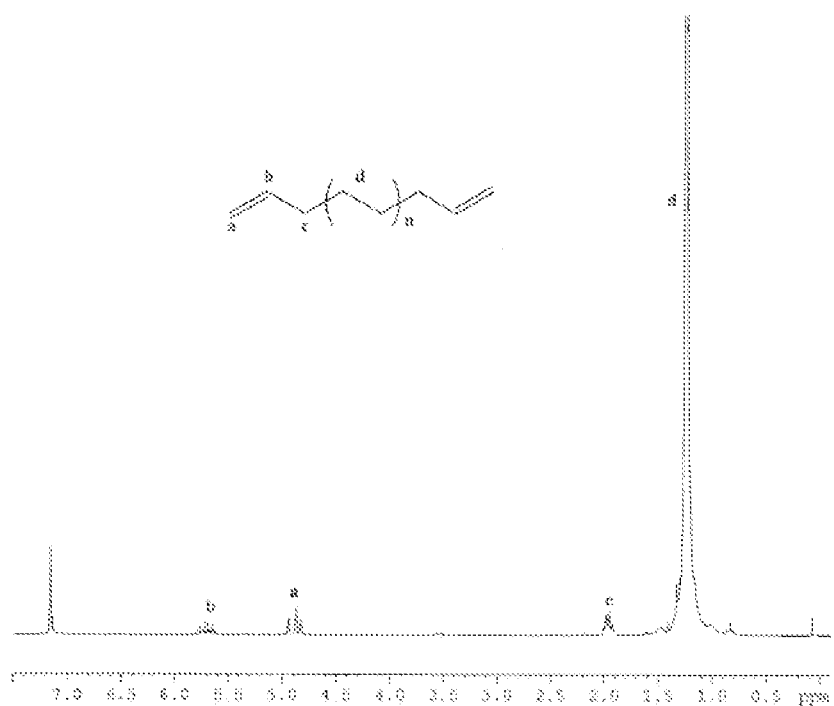
FIG. 5 is the $^1$H NMR (nuclear magnetic resonance) spectrum of the telechelic polyethylene according to the invention, $CH_2=CH-(CH_2)_9-PE-(CH_2)_9-CH=CH_2$, where $PE=(CH_2-CH_2)$.

Characterization:

$^1$H NMR (FIG. 5) (2/1 v/v TCE/C$_6$D$_6$, 400 MHz, 363K) δ ppm=5.70 (m, CH$_2$=CH—CH$_2$—), 4.83-4.93 (m, CH$_2$=CH—CH$_2$—), 1.96 (q, J=7 Hz, CH$_2$=CH—CH$_2$—), 1.24 (br, (CH$_2$CH$_2$)$_n$).

Synthesis 1: $M_n$=1630 g·mol$^{-1}$, $M_w/M_n$=1.27, F=75%.

The invention claimed is:

1. A process for preparing a telechelic polyolefin of formula (I):

(I)

wherein:
A represents a (co)polymer comprising at least 95 mol % of (CH$_2$—CH$_2$) units;
Z is selected from the group consisting of halogens; thiols and their derivatives; azides; amines; alcohols; the carboxylic acid function; isocyanates; silanes; phosphorous derivatives; dithioesters; dithiocarbamates; dithiocarbonates; trithiocarbonates; alkoxyamines; the vinyl function; dienes; and the group -A-(CH$_2$)$_p$—CH=CH$_2$; and
p is a whole number between 1 and 20, said process comprising the following steps:
preparing a compound of formula (II):

(II)

wherein m is 2 or 3; and
when m=2, Y is an alkaline earth metal; and
when m=3, Y is an element of group 13; and
cleaving the bond between Y and A-(CH$_2$)$_p$—CH=CH$_2$, and functionalizing A-(CH$_2$)$_p$—CH=CH$_2$ with Z.

2. A process according to claim 1, wherein the preparing the compound of formula (II) is achieved in the presence of a transition metal or lanthanide complex, and a transfer agent of formula (III):

(III).

3. A process according to claim 2, wherein the transition metal or lanthanide complex is a metallocene selected from the group consisting of compounds of which the formula contains the base structure: (Cp$^1$)(Cp$^2$)M or E(Cp$^1$)(Cp$^2$)M;
M being a group 3 or 4 metal, or a lanthanide; and
Cp$^1$, Cp$^2$ being cyclopentadienyl, fluorenyl or indenyl groups or those groups featuring additional substituents;
E being a bridge between the Cp$^1$ and Cp$^2$ ligands, of the formula M'R$^1$R$^2$, M' being a group 14 element, and R$^1$ and R$^2$ being alkyl or aryl groups having 1 to 20 carbon atoms.

4. A process according to claim 3, wherein the complex is a metallocene of the formula (C$_5$Me$_5$)$_2$MX$_2$Li(OEt$_2$)$_2$, M being a group 3 metal or lanthanide and X being a halogen.

5. A process according to claim 4, wherein M is a lanthanide.

6. A process according to claim 2, wherein the telechelic polyolefin is represented by the formula CH$_2$=CH—(CH$_2$)$_p$—(CH$_2$—CH$_2$)$_n$—I, I being an iodine atom, p being a whole number between 6 and 9, and n being a whole number between 17 and 360.

7. A process according to claim 1, wherein the functionalizing step with Z comprises the addition of a compound selected from the group consisting of iodine I$_2$, sulfur S$_8$ and tetraethylthiuram disulfide.

8. A process according to claim 1, wherein the functionalizing step with Z is an oxidative coupling when Z=-A-(CH$_2$)$_p$—CH=CH$_2$.

9. A process according to claim 1, further comprising, subsequent to the functionalizing with Z, modifying at least one of the chain-ends of the telechelic polyolefin by reaction of the vinyl function and/or of the Z group.

10. A process according to claim 1, wherein, when m=2, Y is magnesium or zinc, and when m=3, Y is aluminum.

11. A process according to claim 1, wherein p is a whole number between 6 and 9.

12. A process according to claim 1, wherein the telechelic polyolefin is represented by the formula CH$_2$=CH—(CH$_2$)$_p$—(CH$_2$—CH$_2$)$_n$—I, I being an iodine atom, p being a whole number between 6 and 9, and n being a whole number between 17 and 360.

13. A telechelic polyolefin of formula (I):

(I)

wherein:
A represents a (co)polymer comprising at least 95 mol % of (CH$_2$—CH$_2$) units;
Z is selected from the group consisting of halogens; thiols and their derivatives; azides; amines; alcohols; the carboxylic acid function; isocyanates; silanes; phosphorous derivatives; dithioesters; dithiocarbamates; dithiocarbonates; trithiocarbonates; alkoxyamines; and dienes; and p is a whole number between 1 and 20.

14. A telechelic polyolefin according to claim 13, wherein the $CH_2=CH-(CH_2)_p-$ group of formula (I) originates from a transfer agent of formula $Y((CH_2)_p-CH=CH_2)_m$, wherein m is 2 or 3; and when m=2, Y is an alkaline earth metal; and when m=3, Y is an element of group 13.

15. A telechelic polyolefin according to claim 13, wherein A is a linear polyethylene of formula $(CH_2-CH_2)_n$, n being a whole number between 7 and 3600.

16. A telechelic polyolefin according to claim 13, wherein the telechelic polyolefin is represented by the formula $CH_2=CH-(CH_2)_p-(CH_2-CH_2)_n-I$, I being an iodine atom, p being a whole number between 6 and 9, and n being a whole number between 17 and 360.

17. A telechelic polyolefin according to claim 13 wherein p is a whole number between 6 and 9.

\* \* \* \* \*